US010626170B2

(12) United States Patent
Rabbani

(10) Patent No.: US 10,626,170 B2
(45) Date of Patent: *Apr. 21, 2020

(54) SULFONATED SCLEROSTIN, ANTIBODIES, EPITOPES AND METHODS FOR IDENTIFICATION AND USE THEREFOR

(71) Applicant: Enzo Biochem, Inc., New York, NY (US)

(72) Inventor: Joshua Rabbani, New York, NY (US)

(73) Assignee: Enzo Biochem, Inc., New York, NY (US)

(*) Notice: Subject to any disclaimer, the term of this patent is extended or adjusted under 35 U.S.C. 154(b) by 241 days.

This patent is subject to a terminal disclaimer.

(21) Appl. No.: 15/447,496

(22) Filed: Mar. 2, 2017

(65) Prior Publication Data

US 2017/0198033 A1 Jul. 13, 2017

Related U.S. Application Data

(62) Division of application No. 12/802,447, filed on Jun. 7, 2010, now Pat. No. 9,617,323.

(51) Int. Cl.
C07K 16/22 (2006.01)
C07K 14/47 (2006.01)
C07K 14/705 (2006.01)
C07K 14/71 (2006.01)
C07K 16/44 (2006.01)
C07K 14/51 (2006.01)

(52) U.S. Cl.
CPC ............ C07K 16/22 (2013.01); C07K 14/47 (2013.01); C07K 14/51 (2013.01); C07K 14/705 (2013.01); C07K 14/71 (2013.01); C07K 16/44 (2013.01); C07K 2317/34 (2013.01)

(58) Field of Classification Search
None
See application file for complete search history.

(56) References Cited

U.S. PATENT DOCUMENTS

| | | | |
|---|---|---|---|
| 4,895,452 A | 1/1990 | Yiournas et al. | |
| 4,921,706 A | 5/1990 | Roberts et al. | |
| 7,381,409 B2 * | 6/2008 | Winkler | C07K 14/51 424/139.1 |
| 7,585,501 B2 | 9/2009 | Krumlauf et al. | |
| 9,403,882 B2 * | 8/2016 | Rabbani | C07K 14/47 |
| 9,493,541 B2 | 11/2016 | Rabbani | |
| 9,617,323 B2 | 4/2017 | Rabbani | |
| 2004/0009535 A1 | 1/2004 | Brunkow | |
| 2004/0038860 A1 | 2/2004 | Allen et al. | |
| 2005/0163776 A1 | 7/2005 | Raven et al. | |
| 2005/0196349 A1 | 9/2005 | Wu et al. | |
| 2006/0030523 A1 | 2/2006 | Wu et al. | |
| 2006/0127393 A1 | 6/2006 | Li et al. | |
| 2006/0198791 A2 | 9/2006 | Wu et al. | |
| 2006/0233801 A1 | 10/2006 | Brunkow | |
| 2007/0110747 A1 | 5/2007 | Paszty et al. | |
| 2007/0154472 A1 | 7/2007 | Widom et al. | |
| 2007/0299009 A1 | 12/2007 | Dong et al. | |
| 2008/0119402 A1 | 5/2008 | Zheng et al. | |
| 2009/0130113 A1 | 5/2009 | Kneissel et al. | |
| 2010/0298200 A1 | 11/2010 | Liu et al. | |
| 2011/0300159 A1 | 12/2011 | Rabbani | |
| 2012/0071399 A1 | 3/2012 | Rabbani et al. | |

FOREIGN PATENT DOCUMENTS

| | | |
|---|---|---|
| WO | WO2005/003158 | 1/2005 |
| WO | WO2005003158 | 1/2005 |
| WO | WO2005/095448 | 10/2005 |
| WO | WO2006/119107 | 11/2006 |
| WO | WO2011/156252 | 12/2011 |
| WO | WO2012/058393 | 5/2012 |

OTHER PUBLICATIONS

Ruben et al., AB023445 Standard: Peptide; 15 AA, XP-002758468, Amino acid sequence #85 associated with human secreted proteins (Sep. 4, 2003).
Skolnick et al., "From genes to protein structure and function: novel applications of computational approaches in the genomic era," TIBTECH, vol. 18, pp. 34-29 (2000).
Attwood, Teresa K., "The Babel of Bioinformatics," Science, vol. 290, pp. 471-473 (2000).
Chen et al., "Activation of the Wnt Pathway Plays a Pathogenic Role in Diabetic Retinopathy in Humans and Animal Models," Am. J. Pathol., vol. 175, pp. 2676-2685 (2009).
Gregory et al., "Dkk-1-derived Synthetic Peptides and Lithium Chloride for the Control and Recovery of Adult Stem Cells from Bone Marrow," J. Biol. Chem., vol. 280, pp. 2309-2323 (2005).
Kasinathan et al., "Inhibition of Tyrosylprotein Sulfotransferase by Sphingosine and its Reversal by Acidic Phospholipids," Biochemistry, vol. 32, pp. 1194-1198 (1993).
Kasinathan et al., Effect of Sofalcone on Tyrosylprotein Sulfotransferase, Gen. Pharmacol, vol. 25, pp. 2017-1020 (1994).
Lee et al., "Intranasal delivery of proteins and peptides," Bioharm., pp. 30-37 (1988).

(Continued)

Primary Examiner — Sharon X Wen
(74) Attorney, Agent, or Firm — Paul Diamond, Esq.

(57) ABSTRACT

Provided are antibodies that bind to: a sulfonated epitope of the protein Sclerostin, to Sclerostin portions comprising a sulfonated amino acid and to dimerized forms of Sclerostin. Further provided are compositions and peptides comprising a sulfonated epitope of sclerostin. Also provided by this invention are methods for production of such antibodies, both active and passive, and methods for identifying antibodies specific for sulfonation sites in Sclerostin and other antibodies which discriminate between sulfonated and unsulfonated forms of sclerostin. Physical and virtual screening processes are provided in this invention for identifying compounds which disrupt or inhibit sulfonation and the interaction between Sclerostin and binding partners. The antibodies and compositions of the present invention are useful in diagnostic and therapeutic applications directed to Sclerostin-related disorders.

6 Claims, 5 Drawing Sheets

Specification includes a Sequence Listing.

(56) References Cited

OTHER PUBLICATIONS

Moester et al., "Sclerostin: Current Knowledge and Ftuure Perspectives," Calcif. Tissue Int., vol. 87, pp. 99-107 (2010).
Murrills et al., A Cell-Based Dkk1 Binding Assay Reveals Roles for Extracellular Domains of LRP5 in Dkk1 Interaction and Highlights Differences Between Wild-Type and the High Bone Mass Mutant LRP5(G171V), J. Cellular Biochem., vol. 108, pp. 1066-1075 (2009).
Polakis, "Wnt signaling and cancer." Genes Dev., vol. 14, pp. 1837-1851 (2000).
Stevenson, Advances in Peptide Pharmaceuticals, Curr. Phar. Biotechnol., vol. 10, pp. 122-137 (2009).
Woods et al., "Sulfation, the UP-and-Coming Post-Translational Modification: Its Role and Mechanism in Protein-Protein Interaction," J. Proteome Res., vol. 6, pp. 1176-1182 (2007).
Weidauer et al. NMR structure of the Wnt modulator protein Sclerostin, BBRC 2009, 160-165, 380.
Westmuckett et al., Early postnatal pulmonary failure and primary hypothyroidism in mice with combined TPST-1 and TPST-2 deficiency, Gen. Compar. Endocrine 2008, 145-153, 156.
Winkler et al., Osteocyte control of bone formation via sclerostin, a novel BMP antagonist, EMBO J 2003, 6267-6276, 22.
Winkler et al., Noggin and Sclerostin Bone Morphogenetic Protein Antagonists Form a Mutually Inhibitory Complex, J. Biol. Chem. 2004, 36293-36298, 279.
Chan, Sze Lai Celine, Sclerostin: a negative regulator of bone formation and a target for osteoporosis therapy, Sclerostin : a negative regulator of bone formation and a target for osteoporosis therapy, 2009, 83-84, Ph.D. Thesis, University of Hong Kong.
MacDonald et al., Wnt/beta-catenin signaling: components, mechanisms, and diseases, Developmental Cell, 2009, 9-26, 17.
Zhong et al., Regulation of secreted frizzled-related protein-1 by heparin, JBC 2007, 20523-20533, 282.
Baeuerle and Huttner, Cholorate—A potent inhibitor of protein sulfation in intact cells, BBRC 1986, 870-877, 141.
Baeuerle and Huttner, Tyrosine Sulfation of Yolk Proteins 1, 2, and 3 in *Drosophila melanogaster*, J. Biol. Chem. 1985, 6434-6439, 260.
Banner et al., Crystal Structure of the Soluble Human 55 kd TNF Receptor-Human TNF Beta Complex: Implications for TNF Receptor Activation, Cell, 1993, 431-445, 73.
Borghei et al., Targeted Disruption of Tyrosylprotein Sulfotransferase-2, an Enzyme That Catalyzes Post-translational Protein Tyrosine O-Sulfation, Causes Male Infertility, J. Biol. Chem. 2006, 9423-9431, 281.
Bundgaard et al., New Consensus Features for Tyrosine O-Sulfation Determined by Mutational Analysis, J. Biol. Chem. 1997, 21700-21705, 272.
Bundgaard et al., Analysis of Tyrosine-O-Sulfation, Methods Mol Bio 2008, 47-66, 446.
Cha et al., Wnt11/5a Complex Formation Caused by Tyrosine Sulfation Increases Canonical Signaling Activity, Current Biol 2009, 1573-1580, 19.
Colvin et al., CXCR3 Requires Tyrosine Sulfation for Ligand Binding and a Second Extracellular Loop Arginine Residue for Ligand-Induced Chemotaxis, Molec Cell Biol 2006, 5838-5849, 26.
Cormier et al., Specific interaction of CCR5 amino-terminal domain peptides containing sulfotyrosines with HIV-1 envelope glycoprotein gp120, Proc. Nat. Acad. Sci USA 2000, 5762-5767, 97.
Costagliola et al. Tyrosine sulfation is required for agonist recognition by glycoprotein hormone receptors, EMBO J 2002, 504-513, 21.
Craig et al., Sclerostin binds and regulates the activity of cysteine-rich protein 61, BBRC 2010, 36-40, 392.
Craig et al., Production and Characterization of Monoclonal Antibodies to Human Sclerostin, Hybridoma 2009, 377-381, 28.
Digiovanna et al., Production of Antibodies That Recognize Specific Tyrosine-Phosphorylated Peptides, Current Protocols in Cell Biology 2002, 16.6.1-16.6.18.
Drake and Hortin, Improved detection of intact tyrosine sulfate-containing peptides by matrix-assisted laser desorption/ionization time-of-flight mass spectrometry in linear negative ion mode, Int J Biochem Cell Biol 2010, 174-179, 42.
Farzan et al., Tyrosine Sulfation of the Amino Terminus of CCR5 Facilitates HIV-1 Entry, Cell 1999, 667-676, 96.
Farzan et al., Sulfated Tyrosines Contribute to the Formation of the C5a Docking Site of the Human C5a Anaphylatoxin Receptor, J Exp Med 2001, 1059-1065, 193.
Feng et al., Sulfotyrosines of the Kaposi's Sarcoma-Associated Herpesvirus G Protein-Coupled Receptor Promote Tumorigenesis through Autocrine Activation, J Vir 2010, 3351-3361, 84.
Fieger et al., Type 1 sphingosine 1-phosphate G protein-coupled receptor signaling of lymphocyte functions requires sulfation of its extracellular amino-terminal tyrosines, FASEB J 2005, 1926-1928, 19.
Gao et al., Sulfation of Tyrosine 174 in the Human C3a Receptor is Essential for Binding of C3a Anaphylatoxin, J. Biol. Chem. 2003, 37902-37908, 278.
Gorr and Cohn, Secretion of Sulfated and Nonsulfated Forms of Parathyroid Chromogranin A (Secretory Protein-I), J. Biol. Chem. 1990, 3012-3016, 265.
Gutierrez et al., Analysis of Post-translational CCR8 Modifications and Their Influence on Receptor Activity, J. Biol. Chem. 2004, 14726-14733, 279.
Hammond et al., Beta Strand Peptidomimetics as Potent PDZ Domain Ligands, Chem & Biol 2006, 1247-1251, 13.
Hemmerich et al., Strategies for drug discovery by targeting sulfation pathways, Drug Discovery Today 2004, 967-975, 9.
Hilsted and Rehfeld, alpha-Carboxyamidation of Antral Progastrin, J. Biol. Chem. 1987, 16953-16957, 262.
Hirata et al., Human P-selectin Glycoprotein Ligand-1 (PSGL-1) Interacts with the Skin-associated Chemokine CCL27 via Sulfated Tyrosines at the PSGL-1 Amino Terminus, J. Biol. Chem. 2004, 51775-51782, 279.
Hoffhines et al., Detection and Purification of Tyrosine-sulfated Proteins Using a Novel Anti-sulfotyrosine Monoclonal Antibody, J. Biol. Chem. 2006, 37877-37887, 281.
Hortin et al., Inhibitors of the sulfation of proteins, glycoproteins and proteoglycans, BBRC 1988, 342-348, 150.
Huang and Honda, CED: a conformational epitope database, BMC Immunology 2006, 7:7.
Huttner et al., Determination and Occurrence of Tyrosine O-Sulfate in Proteins, Meth Enzymol 1984, 200-223, 107.
Itkonen et al., Mass spectrometric detection of tyrosine sulfation in human pancreatic trypsinogens, but not in tumor-associated trypsinogen, FEBS Journal 2008, 289-301, 275.
Jekel et al., Dimerization of an antigenic peptide leads to strong interaction with its antibody, Biochimica Biophysica Acta 1996, 195-198, 1291.
Kehoe and Bertozzi, Tyrosine sulfation: a modulator of extracellular protein—protein interactions, Chemistry & Biology 2000, R57-R61, 7.
Kehoe et al., Using Phage Display to Select Antibodies Recognizing Post-translational Modifications Independently of Sequence Context, Molec Cell Proteomics 2006, 2350-2363, 5.
Kehoe et al., Tyrosylprotein sulfotransferase inhibitors generated by combinatorial target-guided ligand assembly, Bioorg Med Chem Letters 2002, 329-332, 12.
Liu et al. Tyrosine Sulfation is Prevalent in Human Chemokine Receptors Important in Lung Disease, Am J Resp Cell Molec Biol 2008, 738-743, 38.
Ma and Geng, Obligatory Requirement of Sulfation for P-Selectin Binding to Human Salivary Gland Carcinoma Acc-M Cells and Breast Carcinoma ZR-75-30 Cells, J Immunol 2002, 1690-1696, 168.
Medzihradszky et al., O-Sulfonation of Serine and Threonine, Molec Cell Proteomics 2004, 429-443, 3.
Mintz et al., Chlorate-induced Inhibition of Tyrosine Sulfation on Bone Sialoprotein Synthesized by a Rat Osteoblast-like Cell Line (UMR 106-01 BSP), J. Biol. Chem. 1994, 4845-4852, 269.
Monigatti et al., Protein sulfation analysis—A primer, Biochim Biophys Acta 2006, 1904-1913, 1764.

(56) References Cited

OTHER PUBLICATIONS

Monigatti et al. The sulfinator: predicting tyrosine sulfation sites in protein sequences, Bioinformatics 2002, 769-770, 18.
Moreau et al., Discontinuous epitope prediction based on mimotope analysis, Bioinformatics 2006,1088-1095, 22.
Niehrs et al., Analysis of the Substrate Specificity of Tyrosylprotein Sulfotransferase Using Synthetic Peptides, J. Biol. Chem. 1990, 8525-8532, 265.
Onnerfjord et al., Identification of Tyrosine Sulfation in Extracellular Leucine-rich Repeat Proteins Using Mass Spectrometry, J. Biol. Chem. 2004, 26-33, 279.
Ouyang et al., Reduced Body Weight and Increased Postimplantation Fetal Death in Tyrosylprotein Sulfotransferase-1-deficient Mice, J. Biol. Chem. 2002, 23781-23787, 277.
Rehfeld et al., Cell-specific processing of pro-cholecystokinin and pro-gastrin, Biochimie 1988, 25-31, 70.
Seibert and Sakmar, Toward a Framework for Sulfoproteomics: Synthesis and Characterization of Sulfotyrosine-Containing Peptides, Biopolymers, 2008, 459-477, 90.
Stone et al., Tyrosine sulfation: an increasingly recognised post-translational modification of secreted proteins, New Biotechnology 2009, 299-317, 25.
Van Regenmortel, From absolute to exquisite specificity. Reflections on the fuzzy nature of species, specificity and antigenic sites, J Immunol Methods 1998, 37-48, 216.
Veverka et al., Characterization of the Structural Features and Interactions of Sclerostin, J. Biol. Chem. 2009,10890-10900, 284.
Villen et al., Synthetic Peptides as Functional Mimics of a Viral Discontinuous Antigenic Site, Biologicals 2001, 265-269, 29.
Chan, Sze Lai Celine, "Sclerostin—A Negative Regulator of Bone Formation and a Target for Osteoporosis Therapy," Thesis for Doctor of Philosophy Degree at the University of Hong Kong (2009).
Cha et al., "Wnt11/5a Complex Formation Caused by Tyrosine Sulfation Increases Canonical Signaling Activity," *Current Biology*, vol. 19, pp. 1573-1580 (2009).
Craig, "Production and Characterization of Monoclonal Antibodies to Human Sclerostin," *Hybridoma*, vol. 28, No. 5, pp. 377-381 (2009).
European Patent Application No. 18173173, European search Report and Information on Search Strategy (2018).
Moester et al., "Sclerostin: Current Knowledge and Future Perspectives," *Calcif Tissue Int*, vol. 87, pp. 99-107 (2010).
Monigatti et al., "The Sulfinator: predicting tyrosine sulfation sites in protein sequences," *Applications Note*, vol. 18, No. 5, pp. 769-770 (2002).
Rider et al., "Bone Morphogenetic protein and growth differentiation factor cytokine families and their protein antagonists," *Biochem J.*, vol. 429, pp. 1-12 (2010).
Seibert et al., "Toward a Framework for Sulfoproteomics: Synthesis and Characterization of Sulfotyrosine-Containing Peptides," *PeptideScience*, vol. 90, No. 3, pp. 459-477 (2007).
Veverka et al., "Characterization of the Structural Features and Interactions of Sclerostin," *Journal of Biological Chemistry*, vol. 284, No. 16, pp. 10890-10900 (2009).
Campbell, "Monoclonal Antibody Technology, Chapter 1, General properties and applications of monoclonal antibodies," Elsevier Science Publishers B.V, pp. 1-32 (1984).
Lloyd et al., "Modelling the human immune response: performance of 1011human antibody repertoire against a broad panel of therapeutically relevant antigens," Protein Engineering, Design & Selection, vol. 22, No. 3, pp. 159-168 (2009).
Baum et al., Bone as a Target Organ in Rheumatic Disease: Impact on Osteoclasts and Osteoblasts, Clinic Rev. Allerg. Immunol., vol. 51, pp. 1-15 (2016).

\* cited by examiner

TO FIG. 1-2 →

Epitopes near sulfonation sites from Example 2

WQAFKNDATEI<u>IPELGEYPEPPPE</u>LENNKTMNRAENGGRPPHHPFETKDVSEYSCRELHFTRYVTDGPCRS
      Amino

AKPVTELVCSGQCGPARLLPNAIGRGKWWRPSGPDFRCIPDRYRAQRVQLLCPGGEAPRARKVRLVASC

KCKRLTRFHNQSELKDFGTEAARPQKGRKPRPRAR<u>SAKANQAELENAY</u>
           Carboxy

Krumlauf (US 7,585,501)

WQAFKNDATEIIPELGEYPEPPPEL<u>ENNKTMNRAENGGRPPHHPFETKDVSEYSCRELHFTRYVTDGPCRS</u>
        Krumlauf #15  Krumlauf #16  Krumlauf #17

AKPVTELVCSGQCGPARLLPNAIGRGKWWRPSGPDFRCIPDRYRAQRVQ<u>LLCPGGEAPRARK</u>VRLVASC
                           Krumlauf #18

KCKRLTRFHNQSELKDFGTEAARPQKGRKPRPRARSAKANQAELENAY

Vervelka et al., 2009

WQAFKNDATEIIPELGEYPEPPPELENNKTMNRAENGGRPPHHPFETKDVSEYSCRELHFTRYVTDGPCRS

AKPVTELVCSG<u>QCGPARLLPNAIGRGKWWRPSGP</u>DFRCIPDRYRAQRVQLLCPGGEAPRARKVRLVASC

KCKRLTRFHNQSELKDFGTEAARPQKGRKPRPRARSAKANQAELENAY

Kneissel et al., US App 2009/0130113

WQAFKNDATEIIPELGEYPEPPPELENNKTMNRAENGGRPPHHPFETKDVSEYSCRELHFTRYVTDGPCRS

AKPVTELVCSGQCGP<u>ARLLPNAIGRGKWWR</u>PSGPDFRCIPDRYRAQRVQLLCPGGEAPRARK<u>VRLVASC</u>
     ID# 156

<u>KCKRLTRF</u>HNQSELKDFGTEAARPQKGRKPRPRARSAKANQAELENAY
ID# 157

Craig et al., 2009

WQAFKNDATEIIPELGEYPEPPPELENNKTMNRAENG<u>GRPPHHPFETKDVSEYSC</u>RELHFTRYVTDGPCRS

AKPVTELVCSGQCGPARLLPNAIGRGKWWRPSGPDFRCIPDRYRAQRVQLLCPGGEAPRARKVRLVASC

<u>KCKRLTRFHNQSELKDFG</u>TEAARPQKGRKPRPRARSAKANQAELENAY

Figure 4
Comparison of Sclerostin epitopes

SULFONATED SCLEROSTIN, ANTIBODIES, EPITOPES AND METHODS FOR IDENTIFICATION AND USE THEREFOR

CROSS REFERENCE TO RELATED APPLICATIONS

This application is a divisional of U.S. application Ser. No. 12/802,447, filed Jun. 7, 2010, which is hereby incorporated by reference in its entirety.

FIELD OF THE INVENTION

This invention relates to the field of immunotherapy, the discovery and application of pharmacological agents, and to the diagnosis and treatment of Sclerostin-related disorders.

All patents, patent applications, patent publications, scientific articles and the like, cited or identified in this application, are hereby incorporated by reference in their entirety in order to describe more fully the state of the art to which the present invention pertains.

BACKGROUND OF THE INVENTION

Although the nature of a protein is dictated primarily by the particular amino acid sequences derived from transcription of its nucleic acid coding sequence, there are post-transcriptional processes that may also affect its properties. Some of these modifications are large scale rearrangements such as: (a) conversion of an inactive pro-enzyme into an active form by removal of part of an amino acid sequence; (b) protease digestion of a composite protein into individual segments with varied functions as seen in some viral proteins (for instance, the polyprotein of HIV); or (c) removal of an internal amino acid sequence (an intein) by protein splicing. In addition to these cleavage processes, modification of individual amino acids can take place by enzymatic addition of functional groups such as methyl, acetyl, phosphate, glycosyl, palmitoyl, sulfonate and ubiquitin groups.

The difference in functionality caused by these modifications can induce radical differences in properties. For instance, proinsulin is an inactive enzyme that is only found in its active form (insulin) after proteolytic cleavage transforms the protein into separate peptide chains connected by disulfide bonds. In another instance, the addition of a ubiquitin moiety doesn't necessarily affect its enzymatic functions but generates a signal for degradation of the "tagged" protein. Even relatively modest alterations, such as acetylation and phosphorylation of one or more amino acids in a protein, can induce remarkable changes in the properties of a protein target. The importance of both of these processes in controlling levels of activities within cells by such modifications can be seen by the abundance of substrate specific versions of each of these family of proteins (acetylases and kinases) within a cell. Further control is exerted by the action of proteins that reverse these changes, i.e., de-acetylases and phosphatases. These modifications can result in an increase or a decrease in the activity level of the target protein and/or a change in its physical locale.

Although the kinase and acetylase modifications are well known areas of research, the importance of sulfonation is receiving increased attention. For recent reviews see Stone et al., 2009 New Biotechnology 25; 299-317 and Monigatti et al., 2006 Biochim Biophys Acta 1764 1904-1913). Sulfonation of Tyrosines is believed to take place in about 1% of the Tyrosines in proteins and appears to facilitate protein-protein interactions (Baeuerle and Huttner 1985 JBC 260; 6434-6439, Kehoe and Bertozzi 2000 Chem Biol 7; R57-R61). Of special interest the connection between sulfonation with receptors and their ligands, since the enzymes, TPST-1 and TPST-2, responsible for sulfonation are localized in the Golgi apparatus. Although these have been observed to be mostly cytokine receptors and their ligands, it has been recently noted that unsulfonated Wnt does not generate as strong a signal as sulfonated Wnt, presumably due to a differential ability of the unsulfonated ligands to bind the LRP5/6 receptors that are involved in the Wnt signaling system (Cha et al., 2009 Current Biol 19; 1573-1580). In addition to Tyrosine, evidence has become available that Serine and Threonine are also potential sites, although at the present time it is not known if this is carried out by the same enzymes (TPST-1 and TPST-2) that modify Tyrosines or if some enzyme or enzymes are responsible (Medzihradszky et al., 2004 Molec Cell Proteomics 3; 429-440).

Testing for the presence of sulfonation modifications in a protein can be carried out using various methods (for reviews, see Monigatti et al. 2006, Stone et al. 2009 and Seibert and Sakmar 2007 Polymer 90; 459-477). The two most popular methods for this type of analysis is the use of mass spectrometry (MS), or antibodies that are specific for Sulfo-Tyr. With regard, to mass spectrometry, definitive answers on the presence of sulfonated Tyrosines can be achieved, but due to the lability of the bond between the sulfonate group and Tyrosine, special modifications have to be made to the standard mass spectrometry protocols (Drake and Hortin, 2010 Int J Biochem Cell Biol 42; 174-179). In a more biological approach, antibodies have been developed that can detect the presence of sulfonated Tyrosine residues. Antibodies have been developed that can detect the presence of sulfonated Tyrosine's regardless of the particular peptide sequence they are embedded within (Kehoe et al., 2006 Molec Cell Proteomics 5; 2350-2363; Hoffhines et al., 2006 J. Biol Chem 281; 37,877-37,887). The general nature of their recognition allows a wide variety of different proteins to be recognized as long as they contain a sulfonated Tyrosine. In many cases, proteins have to be isolated or separated for this type of analysis to observe individual effects, since there is no discrimination between the different sulfonated proteins by such antibodies. For instance, the extent of sulfonation can be determined for individual isolated proteins of interest or patterns of a group of proteins can be analyzed. On the other hand, antibodies have been developed for a specific protein with a sulfonated Tyrosine. These antibodies can detect differences between sulfonated and non-sulfonated forms and can identify the presence of the sulfonated protein in a mixture of other proteins (Bundgaard et al., 2008 Methods Mol Bio 446; 47-66). The specificity of the epitope requires that a new antibody has to be developed for each particular protein of interest.

As information has accumulated concerning the amino acid sequences that are used as substrates for sulfonation, it has become clear that there is no simple consistent recognition sequence (see Niehrs et al., 1990 JBC 265; 8525-8532, Bundgaard et al., 1997 JBC 272; 31,700-31,705 for instance). A computer program called "Sulfinator" has been created recently that is capable of analyzing protein sequences and predicting the presence or absence of sulfonation sites (Monigatti et al. 2002 Bioinformatics 18; 769-770). The program achieves its highest accuracy only when proteins are tested that are either receptors, or ligands for receptors, because these are proteins that are processed through the Golgi apparatus where the TPST-1 and TPST-2 enzymes are localized. Proteins that are cytosolic in nature are physiologically irrelevant since even if they have appropriate sequences they would never come into contact with the Tyrosine sulfotransferases. The Sulfinator does not detect the extent of sulfonation.

In detecting the extent of sulfonation, experiments have shown that even proteins that are substrates for sulfonation do not always represent a homogeneous population with complete sulfonation. For instance, gastrin peptides which are easily sulfonated show a mixed population of both sulfonated and unsulfonated forms in roughly equal proportions (Hilsted and Rehnfeld 1987 JBC 262; 16,953-16,957). In another instance, there may be tissue specific differentiation on the extent of Tyrosine sulfonation of Chromogranin A that depends upon whether it is made in parathyroid or adrenal cells (Gorr and Cohn, 1999, JBC 265; 3012-3016). Different effects have also been observed for proteins such as gastrin/cholecystokinin peptides and their precursors where varying degrees of modification are seen during ontogenesis and pathogenesis of certain diseases (Rehfeld et al., 1989 Biochimie 70; 25-31). Furthermore, in certain circumstances, such as in the expression of cloned recombinant proteins, there may be undersulfonation of proteins that would otherwise be completely modified (Seibert and Sakmar 2008 Biopolymers 90; 459-477).

Although extensive efforts have been made in searching for pharmaceutical agents that affect kinase activity, compounds that affect sulfonation modifications have only recently attracted attention (for instance, see Hemmerich et al., 2004 Drug Discovery Today 9; 967-975). The potential utility of influencing sulfonation reactions can be seen, however, by recent discoveries that CCR5, one of the receptors for recognition of HIV, is sulfonated. The importance of this modification can be seen by results with chlorate (an inhibitor of Tyrosine sulfonation), where the presence of this factor decreases the affinity of gp120/CD4 complexes towards the CCR5 receptor (Farzan et al., 1999 Cell 96; 667-676). Although there are instances where the presence of a sulfonation modification may enhance binding, there are also numerous instances where there is actually an absolute requirement for sulfonation to have taken place in order for certain proteins to have biological activity (Farzan et al., 2001 J Exp Med 193; 1059-1065, Costaglia et al. 2002 EMBO J 21; 504-513, Gao et al., 2003 JBC 278; 37902-37908, Gutierrez et al., 2004 JBC 279; 14726-14733, Hirata et al., 2004 JBC 279; 51775-51782, Fieger et al., 2005 FASEB J 19; 1926-1928 and Colvin et al., 2006 Molec Cell Biol 26; 5838-5849).

Furthermore, in vitro studies also show the importance of sulfonation with regard to binding of gp120/CD4 complexes with CCR5 peptides (Cormier et al., 2000 Proc. Nat. Acad. Sci USA 97; 5762-5767). As such, it has been recognized that the disruption of the sulfonation of CCR5 may be a treatment for HIV infection and disease processes. In another example, Liu et al. 2008 (Am J Resp Cell Molec Biol 38; 738-743) hypothesized that sulfonation was a general feature of cytokine receptors and found that at least 10 different cytokine receptors that are involved in asthma and chronic obstructive pulmonary disease (COPD) are sulfonated. On this basis, the authors concluded that incorporation of this discovery into the structural design of receptor antagonists might show value in the development of effective drug therapies for asthma, COPD and similar inflammatory lung diseases.

Changes in sulfonation patterns have also been found for tumour derived enzymes (Itkonen et al., 2007 FEBS Journal 275; 289-301 and a dependency on sulfonation has been shown for binding of P-selectin to cancer cells (Ma and Geng 2002 J Immunol 168; 1690-1696) and tumorigenesis (Feng et al., 2010 J Vir 84; 3351-3361).

SUMMARY OF THE INVENTION

The present invention is based upon the discovery that Sclerostin possesses post-translational modifications where at least two amino acids are sulfonated in vivo. It is known that sulfonation modifications are frequently involved in protein-protein interactions and as such, it has been found that Sclerostin exhibits sulfonation-dependent alterations in a variety of biological properties that are likely derived from protein-protein interactions. These include effects on the binding of Sclerostin to the LRP5 receptor as well as differential effects upon Wnt signaling as judged by inhibition of blockage by various amounts of Sclerostin on the induction of alkaline phosphatase by Wnt. The discovery of modifications of these proteins allows recognition of previously unknown epitopes that can be used as the basis for the selection of antibodies against the sulfonated regions of these proteins for diagnostic or therapeutic purposes.

Thus, in one particular embodiment of the present invention, antibodies are isolated or produced that recognize the sulfonated portions of Sclerostin. The antibodies may be specific for epitopes where the amino acid is sulfonated. Alternatively, the antibody may recognize and bind only to epitopes where the amino acid remains unsulfonated.

In another embodiment of the present invention, antibodies are isolated or produced that recognize the sulfonation region of Sclerostin, regardless of whether the amino acid in this target region is sulfonated or not. The antibodies of the present invention may be used alone or in conjunction with other previously described antibodies to Sclerostin that may be specific to regions that do not comprise sulfonation modification sites.

Another embodiment of the present invention is directed towards diagnostic utility, where the potential dependency of biological properties on the presence or absence of sulfonation in these sites would allow evaluation of clinical properties that may depend upon the degree of sulfonation of these proteins. This may be used for the identification of a disease condition or used to monitor the effects of a therapeutic program.

In another embodiment of the present invention, antibodies against the sulfonate modified regions of Sclerostin may be administered to block or interfere with binding of Sclerostin with an interacting protein, thereby reducing the functional activity of Sclerostin in a subject and providing beneficial effects.

Furthermore, in another embodiment of the present invention, the discovery of a linkage between the sulfonation state of Sclerostin and biological activity presents an opportunity to use the sulfonated regions as targets for intervention, where pharmaceutical compounds may be used to affect the degree of sulfonation and thereby modulate the biological activity of Sclerostin.

In another aspect of the present invention, potential differential effects of therapeutic compounds on sulfonated or unsulfonated forms of Sclerostin may now be addressed due to the discovery of sulfonation modifications in Sclerostin. Consequently, virtual screening processes for identification of compounds that bind to selected sites on Sclerostin may now be carried out where the virtual model of the target molecule includes a substitution of the sulfonated amino acid for the unmodified form in Sclerostin, thereby altering projected binding affinities when compounds are screened.

Another embodiment of the present invention makes use of the fact that sulfonation modifications are usually involved in protein-protein interactions, and as such, the identification of sulfonation modification sites in Sclerostin serves as an indication that these regions can be indentified as previously unknown sites that participate in interactions with other protein molecules. Therefore, in another embodiment of the present invention, the synthesis of peptides that comprise the sulfonation region may have utility as modulators, altering the ability of Sclerostin to interact with its binding partners. In carrying out such a role, both sulfonated and unsulfonated forms of such peptides may provide utility.

Lastly, interactions between Sclerostin and a binding partner are usually described in the context of heterodimeric complexes such as Sclerostin/LRP or Sclerostin/BMP receptor. It is a further consideration of the present invention, however, that the discovery of sulfonation modifications may have ramifications with regard to homodimeric complexes that may take place between two Sclerostin monomeric units.

BRIEF DESCRIPTION OF THE FIGURES

FIGS. 1-1A through 1-2C disclose SEQ ID NOS: 9 and 7, respectively, in order of appearance.

FIG. 2 are results of treatment of Sclerostin with TPST-1 and a subsequent comparison between treated and untreated Sclerostin with regard to binding to the LRP5 receptor.

FIG. 4 is a comparison between epitopes defined by Sulfonation sites of Sclerostin and epitopes previously described in the literature. FIG. 4 discloses all sequences as SEQ ID NO: 10.

DESCRIPTION OF THE INVENTION

Figures 1, 1A:
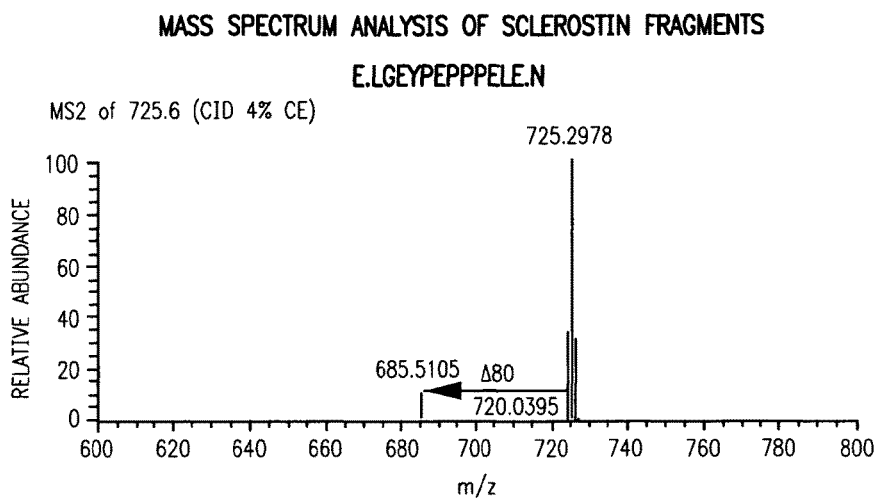
FIGS. 1-1A, 1-1B, 1-1C, 1-2A, 1-2B and 1-2C show the identification of sulfonated Tyrosines in Sclerostin by mass spectrometry.
Figures 1, 1B:
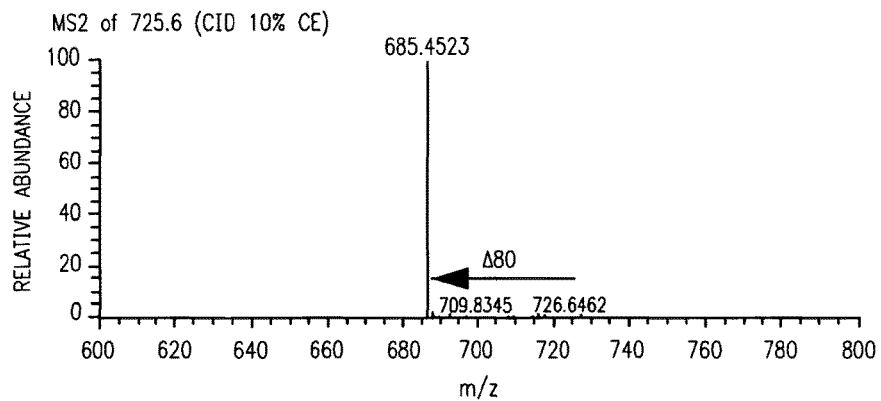
Figures 1, 1C:
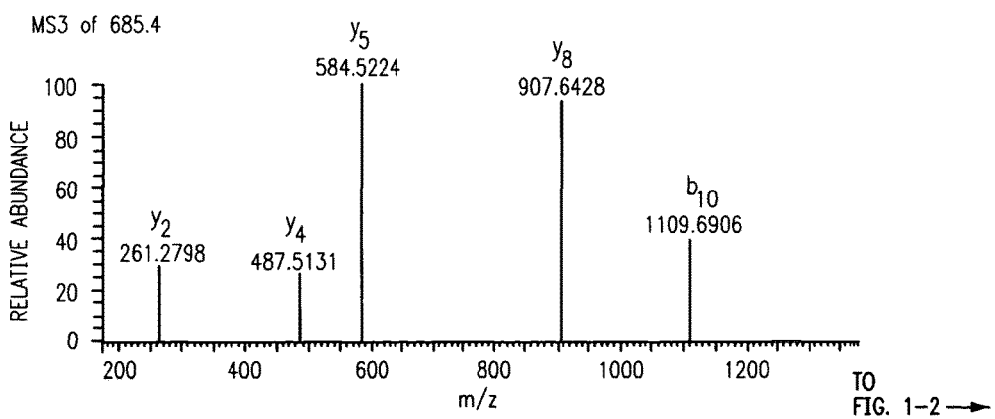

The present invention describes the discovery that Sclerostin, a ligand of various LRP receptors, can be sulfonated in at least two different sites, $Tyr_{43}$ and $Tyr_{213}$ (using the UniProtKB Accession No. Q9BQB4 of unprocessed Sclerostin as reference points). A further discovery is that an ex vivo sulfonation treatment of a preparation of recombinant Sclerostin results in an increase in the affinity of the Sclerostin to the LRP5/6 receptor as well as an increase in its ability to suppress Wnt induced expression of Alkaline Phosphatase. Various means may be employed to determine the presence of sulfonation modifications in proteins of interest. As described in Example 2 below, mass spectrometry (mass spec) analysis was carried out using Sclerostin that was expressed in cells capable of carrying out post-synthetic modifications such as sulfonation. It should be noted that the standard conditions that are usually employed in mass spec studies leads to a rapid loss of sulfonate groups. As such, when detection of sulfonated targets is desired, avoidance of acidic conditions and lower energy inputs are required in order to increase the sensitivity of detection of sulfonated Tyrosines in specimens of interest (Drake and Hortin, 2010). This type of analysis may lead to the identification of the presence of sulfonated Tyrosines and in many cases the exact position of the sulfonated amino acid. A caveat to be considered is that the simultaneous presence of both sulfonated and unsulfonated Tyrosines for a given fragment does not give any estimate for their relative proportions prior to analysis since the process is still liable to losses of sulfonate moieties, thereby generating some unsulfonated Tyrosines de novo. Distinguishing between pre-existing and converted unsulfonated Tyrosines is problematic and as such, mass spec serves best as a qualitative tool for whether sulfonation occurs at all at a given site.

Prior to carrying out the mass spec analysis, some of the Sclerostin was used in a reaction with TPST-1 (Example 1) such that if any Tyrosine modification sites were present in the sample they could be converted into a modified from. As described in the mass spec analysis described in Example 2, the presence of sulfonation modifications was found in both the treated and untreated samples of Sclerostin, indicating that the recombinant Sclerostin being tested had undergone sulfonation modifications prior to secretion from the cells used for recombinant expression. As noted above, however, the mass spec analysis can determine the presence of sulfonation modifications, but is unable to provide information on whether there is complete or partial modification on the sulfonation sites. A protein having the appropriate sulfonation sequence may be a candidate for post-synthetic modification as it passes through the Golgi apparatus prior to secretion outside of a cell, but recombinant expression systems are essentially abnormal states and there may be undersulfonation of sites that normally would be fully converted.

Figures 1, 2, 2A:
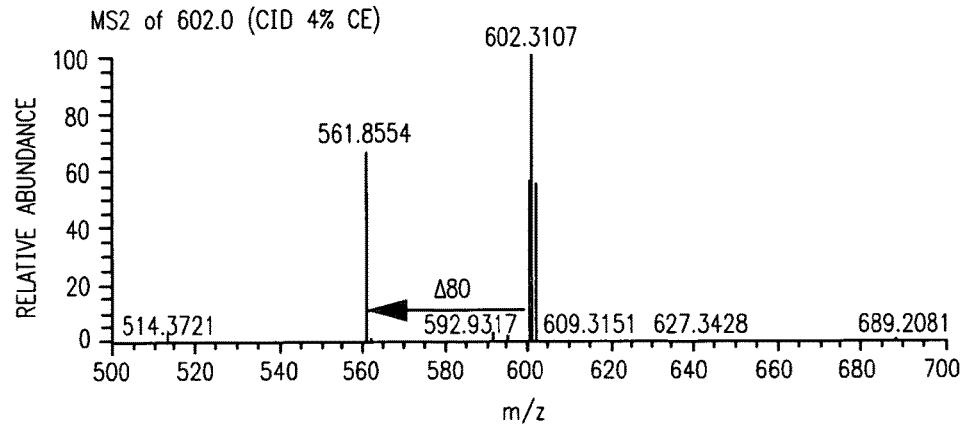
Figures 1, 2, 2B:
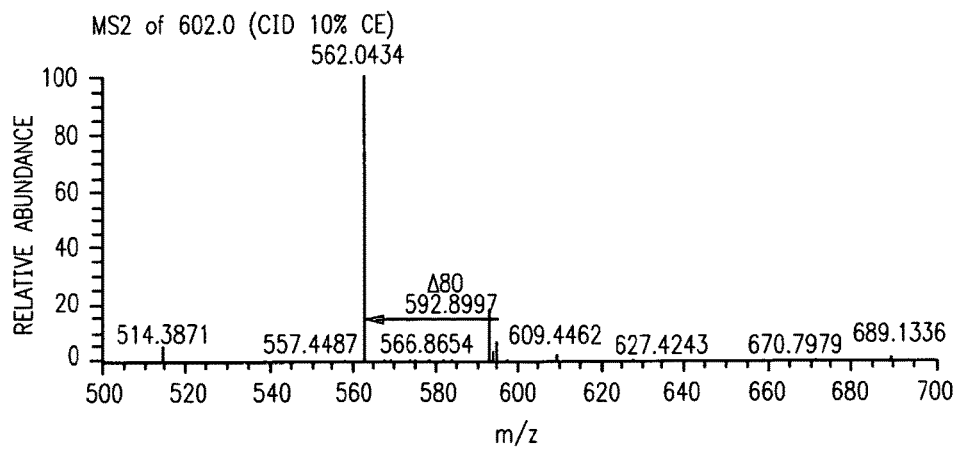
Figures 1, 2, 2C:
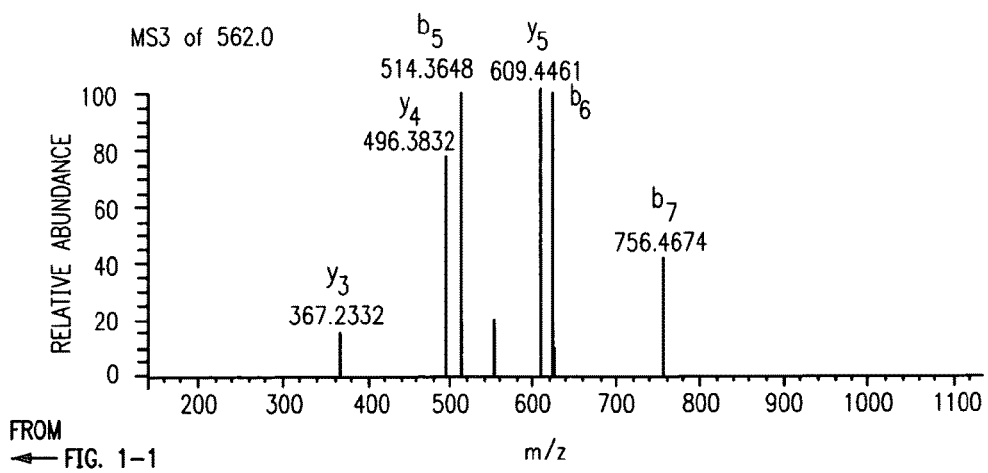
Figure 2:
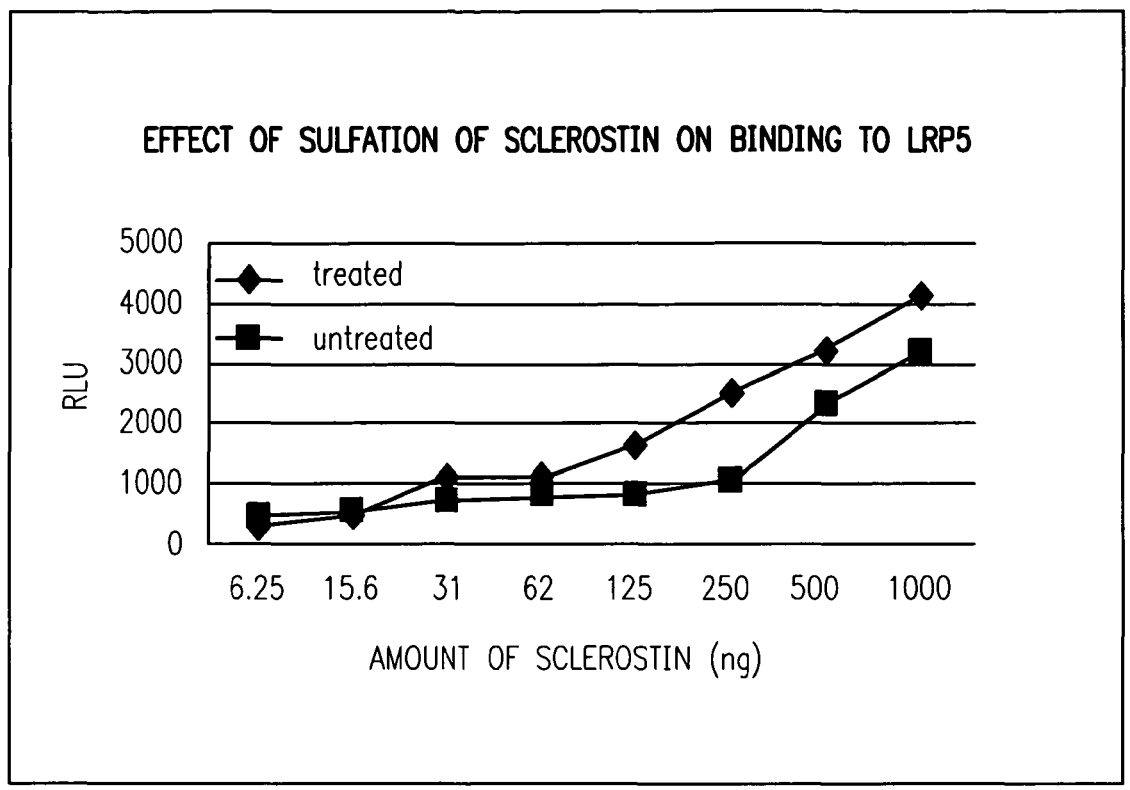
Figure 3:
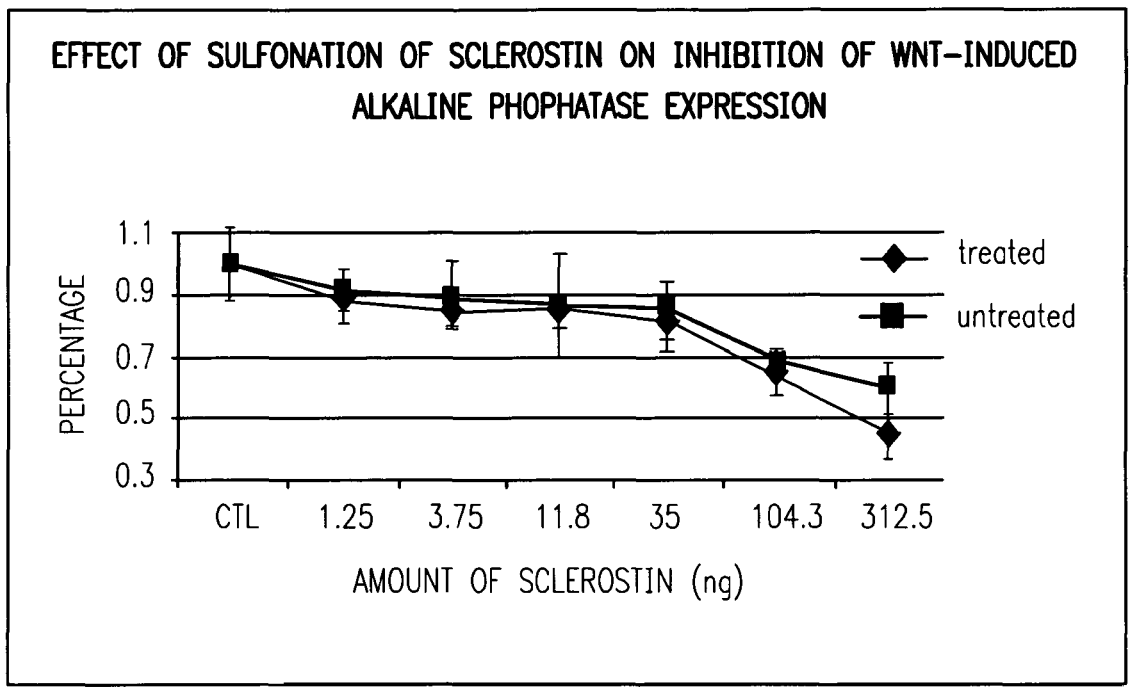
FIG. 3 shows the differential effects produced by treated and untreated Sclerostin with regard to Wnt-induced Alkaline Phosphatase expression.

As such, treated and untreated Sclerostin has been used in biological assays to investigate whether there were any differences in the properties of Sclerostin after an in vitro treatment. As described in Example 3 and as shown in FIGS. 2 and 3, the differences seen with the in vitro treatment are consistent with a conclusion that some Tyrosines in the sulfonation sites of the recombinant Sclerostin passed through without being modified prior to secretion from cells, thereby making them available for in vitro modification and consequently the converted Sclerostins displayed an increased affinity for their binding partners, i.e., the original sample contains partially sulfonated Sclerostin and the treated sample has an increased level of sulfonation. This effect could likely be seen more dramatically if conditions were used such that a comparison was made with starting material that was completely or mostly lacking in sulfonation modifications prior to an in vitro reaction. Ways that this could be accomplished are the use of yeast or bacterial expression systems, treatment of recombinant expression cells with chlorate prior to harvesting the protein or expression in cells that have been mutated to eliminate TPST activity such as those described by Westmuckett et al., 2008, Gen. Compar. Endocrine 156:145-153. With regard to the chlorate treatment, it has been previously shown that such treatment can strongly reduce the degree of sulfonation in cells (Baeuerle and Huttner 186 BBRC 141; 870-877; Hortin et al., 1988 BBRC 150; 342-348; Mintz et al., 1994 J Biol Chem 269; 4845-4852) and a bacterial or yeast host would lack any sulfonation since they intrinsically lack the sulfotranferases responsible for Tyrosine sulfonation (Kehoe and Bertozii 2007 Chemistry & Biology 7; R57-R61).

A further method of investigation is the use of a software program called Sulfinator that can predict the presence of a sulfonation site with 98% accuracy from the amino acid sequence alone. When the sequences from Sclerostin were analyzed with this program, it successfully identified the amino terminal modification of Sclerostin at $Tyr_{43}$ detected by MS analysis but missed the carboxy terminal modification at $Tyr_{213}$. The failure in predictability is likely due to the Tyrosine in Sclerostin that is modified at the carboxy end of Sclerostin being the terminal amino acid itself; since the Sulfinator program uses the neighboring sequences surrounding a Tyrosine for evaluating its likelihood of being sulfonated, by definition, a terminal Tyrosine of Sclerostin would intrinsically lack sequences on one side. It should be pointed out that although the presence of a site predicted to be a sulfonation site is likely dependable, there are incidents where sulfonation modifications were unrecognized by the Sulfinator program but later identified in physical studies (Onnerfjord et al., 2004 JBC 279; 26-33, Hoffhines et al., 2006 JBC 281; 37877-37887). Nonetheless, the recognition of the $Tyr_{43}$ modification by the Sulfinator program is an independent confirmation of the sulfonation of this particular amino acid in Sclerostin.

It should be understood that although sulfonated Tyrosines have been observed in many secreted ligands and their receptors, their presence is not necessarily required and it is inappropriate to make any predictions about their presence in the absence of any investigational analysis. As noted above, it has been estimated that ~1% of the Tyrosines in cellular proteins are modified Tyrosines (Huttner 1984 Methods Enzymol 107; 200-223) which in turn has the implication that ~99% of them would not have this modification.

The discovery that Sclerostin, which participates in the Wnt signaling system, has modified amino acids offers unique methods of analysis as well as therapeutic means. As described in earlier related patent applications (2005/0196349; 2006/0030523; 2008/0119402, hereby incorporated by reference), compounds that block the interaction between LRP5/6 receptors and the Dkk and Sclerostin ligands can offer a variety of useful therapeutic means. Since it has now been discovered that the amino acid sequence of Sclerostin can also comprise a post-synthetic sulfonation modification, compounds that have been previously tested for effects on Sclerostin with regard to Wnt signaling may be retested using separate reaction mixtures or binding assays where either the modified or unmodified versions of these proteins are tested separately. As has been pointed out earlier, some proteins exist as a mixture of sulfonated and unsulfonated forms and previous experiments may have been based upon such a mixture, without recognition that the net effects might be a composite of the individual effects on modified and unmodified Sclerostin. Control over the particular form (sulfonated or unsulfonated) of Sclerostin will now allow investigation into whether compounds are more or less effective with regard to using sulfonated or unsulfonated versions of Sclerostin in assays. The lack of recogntion of the potential presence of a mixture of different forms also allows for the possibility that some effective compounds may have been missed due to the use of Sclerostin preparations that had a preponderance of one form over another.

Furthermore, the presence of a site that is involved in protein-protein interactions is in itself a potential therapeutic target. Thus, a series of compounds can be surveyed to see if they specifically interrupt in vitro or in vivo sulfonate modification of the Tyrosines in Sclerostin. Such pharmaceutical agents would have the potential for modifying the level of activity induced by Sclerostin by controlling the degree of sulfonation and thereby their affinity in protein-protein interactions. Pharmaceutical reagents that may be used to disrupt sulfonation processes can include but not be limited to small molecules, peptides, organic molecules, cyclic molecules, heterocyclic molecules, lipids, charged lipids, glycolipids, polar lipids, non-polar lipids and aptamers. The compounds may be ones that have been designed to bind to the surface of Sclerostin through a virtual screening process as described in US Patent Application No. 2005/0196349. Contrariwise, compounds may be tested independently from virtual screening and tested strictly on a random basis or they may be selected to have a physical resemblance to compounds that result from virtual screening processes. In this process, a revised virtual structure of sclerostin may be devised to takes into consideration the presence of the sulfonation of amino acids. Such a process can also include the use of mutational substitutions at the modification sites (see, for instance, Wu et al., 2005/0196349). Thus, a series of (selected or random) compounds may be assayed for an ability to eliminate or reduce sulfonation of Sclerostin, by any means that have previously been described for analysis and/or detection of sulfonation of proteins. As a control, one or more proteins that also have sulfonation sites may be included to insure that the blockage of sulfonation is specific for the target of interest. Any means that have been described in the past for detection of the presence of sulfonated Tyrosines may be used in this aspect of the present invention, thus for example, these means may be as complex as carrying out MS analysis to simpler methods such as incorporation of $^{35}S$ PAPS by TPST, immunoassays that use antibodies that recognize proteins with sulfonated Tyrosines irrespective of their context (Kehoe et al., 2006 and Hoffhines et al., 2006), or antibodies that are specific for the sulfonated or unsulfonated forms of Sclerostin (as will be discussed in more detail below). If desired, truncated versions of Sclerostin that comprise the target area of interest may also be used as substrates in assays as long as their biological structures/functions are similar to the parent protein. In addition, peptides that may represent the sulfonation site of Sclerostin may also be used for evaluation.

Investigations into compounds that might interrupt sulfonation of proteins has been previously described by Hortin et al., 1988 BBRC 150; 342-348 where compounds were found that were non-specific in that they inhibited sulfonation of proteins, oligosaccharides and proteoglycans (although with varying efficiencies). A similar study has been done more recently by Kehoe et al., 2002 (Bioorg Med Chem Letters 12; 129-132) where two compounds were identified that inhibited sulfonation by TPST-2. Similar to the results published earlier by Hortin et al., further testing showed that the inhibitors affected other sulfotransferases as well. Even if these inhibitors only affected the TPST reaction itself, however, this approach would indiscriminately block sulfonation of a wide variety of different protein targets and thereby lead to potentially toxic effects. It should be noted that knockout mice lacking either TPST-1 (Ouyang et al., 2002 JBC 277; 23,731-23,787) or TPST-2 (Borghei et al., JBC 281; 9423-9431) activity are essentially viable but exhibit a variety of pleiotropic defects. Partial overlap in the functionality of the two TPST enzymes can be seen by experiments with a double knockout that is missing both TPST-1 and TPST-2 where most progeny died soon after birth and any survivors failed to thrive (Westmuckett et al., 2008). These double knockouts exemplify a situation that may be more akin to the presence of a general TPST inhibitor. In addition, as noted previously, there are many proteins involved in protein-protein interactions where sulfonation is obligatory for biological activity and some are involved in inflammatory responses that require sulfonation for functionality; as such, it may be that the double knockouts are phenotypically silent except under certain conditions where such responses would be induced or required. Targeting the modification of a particular sulfonation target as described in the present invention is likely to be superior to efforts to block sulfonation in general since it is likely to have more specific effects than a general blockage that may produce deleterious as well as beneficial effects.

The identification of peptide sequences comprising a modified Tyrosine also allows the use and design of artificial peptides that contain these modifications. Presumably these should have higher binding affinities than their unmodified counterparts. Binding of these peptides to the protein that normally interacts with the complete protein may produce a variety of effects. For instance, some of these peptides could act in a positive fashion by invoking the same response that the intact protein induces. Contrariwise, the peptide could act as a competitive inhibitor and prevent the intact protein from binding. For example, a peptide with sequences from either the carboxy or amino end could reduce the ability of Sclerostin to bind to a LRP receptor. Although the sulfonated peptide would be the basis for the design, it is understood that the actual components can be artificial equivalent of these peptides. Examples of compounds made with such components can comprise but not be limited to the peptide mimetics described in related pending U.S. patent application Ser. No. 11/097,518, as well the substitution of dextro isomers instead of the normal levo forms and peptidomimetics such as those described in Hammond et al., 2006 Chem & Biol 13; 1247-1251. Other examples of analogs that may find use with the present invention are "unnatural amino acids" where in it is understood that in the context of the present invention "unnatural amino acids" refers to amino acids that are not genetically encoded i.e. they are not represented by a nucleotide triple codon. This would include the dextro isomers discussed above as well as other amino acids such as Aib (amino-isobutyric acid), bAib (3-aminoisobutyric acid), Nva (norvaline), β-Ala, Aad (2-aminoadipic acid), bAad (3-am inoadipic acid), Abu (2-am inobutyric acid), Gaba (γ-aminobutyric acid), Acp (6-aminocaproic acid), Dbu (2,4-diaminobutyric acid), TMSA (trimethylsilyl-Ala), aIle (allo-Isoleucine), Nle (Norleucine), tert.Leu, Cit (Citrulline), Orn, Dpm (2,2'-diaminopimelic acid), Dpr (2,3-diaminopropionic acid), α- or β-Nal, Cha (cyclohexyl-Ala), hydroxy-proline, Sar (Sarcosine) etc., cyclic amino acid units and $N^\alpha$-alkylated amino acid units, e.g. MeGly ($N^\alpha$-Methyl-glycine), EtGly ($N^\alpha$-ethylglycine) and EtAsn ($N^\alpha$-ethyl-asparagine). Accordingly, synthetic peptides can be made that include one or more of these unnatural amino acids.

Another series of reagents that may be effective are antibodies directed to the sulfonation site. In the first place, the identification of the sulfonation site offers evidence that the site is likely to be involved in protein-protein interactions. Thus, for instance, the particular portion of the Sclerostin protein involved in interaction with LRP5/6 has not been clearly identified, but the discovery of the sulfonation site of Sclerostin in the amino terminal sequences described in Example 2 provides a novel target for antibody binding that might affect the interaction of Sclerostin with LRP5/6 that is different from the Sclerostin sequences previously postulated by Ververka et al., 2009 JBC 284; 10,890-10,900, Weidauer et al., 2009 BBRC 380; 160-165 and Krumlauf in U.S. Pat. No. 7,585,501. In one embodiment of the present invention, an epitopes is five amino acids or greater. In another embodiment, the epitope encompasses ten or more amino acids. A comparison of the identity and location of potential epitopes of the present invention and sequences used as epitopes in prior art is given in FIG. 4. The underlined regions adjacent to $Tyr_{43}$ and $Tyr_{213}$ in FIG. 4 are only intended to render a visual aid in comparing the regions of the present invention with previously described art and not intended to delineate the epitope itself. Antibodies may be generated that are specific for either the sulfonated or unsulfonated form of Sclerostin and include either $Tyr_{43}$ or $Tyr_{213}$ as part of their epitope. Utility may also be found for antibodies that do not distinguish between the sulfonated and unsulfonated forms, but are still specific for the surrounding amino acids at the Sclerostin sulfonation site. The foregoing antibodies may find use as therapeutic reagents that disrupt interaction between Sclerostin and LRP5/6 as well as other binding partners of Sclerostin. In the case of antibodies that are specific for either sulfonated or unsulfonated forms, a finer degree of control can be exerted over physiological processes, since each type of antibody will be directed towards a subpopulation of the target protein. As such, an ability to target only the sulfonated form will leave the activity of the unsulfonated from intact and vice versa for an antibody to the unsulfonated from. This is a level of discrimination that would not be produced by antibodies described previously for Sclerostin. On the other hand, an antibody of the present invention that is generic in the sense of being independent of the sulfonation state of Sclerostin, may also have therapeutic utility because the sites where modifications take place may have more significance than previously recognized, and thus, these regions are novel epitopes that are useful as targets for immunotherapy.

Development and isolation of antibodies that are targeted to the sulfonation regions discovered and described in the present invention may be carried out by any of the means that have been described previously, including those taught in Bundgaard et al., 2008; Hoffhiner et al., 2006; Kehoe et al. 2006, Craig et al., 2009 Hybridoma 28; 377-381; U.S. Pat. No. 7,585,501, US Patent Application 2004/0009535 and US Patent Application 2009/02130113, all of which are incorporated by reference. One source of antigens that may be used for this purpose can be artificial peptides that represent the sulfonated sequences; these can be obtained from a wide variety of commercial sources that provide custom made peptides. The peptide or peptides used for immunization may be modified or unmodified, depending upon whether the antibody is desired to recognize the modified or unmodified epitope. Post-synthetic modifications can be carried out either chemically or by in vitro modification by TPST-1. Screenings of antibody libraries can then be carried out to determine the nature of the recognition such that it is specific for the sulfonated version of the target protein, the unsulfonated form or is independent of the state of sulfonation. In addition to such custom libraries, pre-existing libraries such as the HuCal phage library is commercially available from AbD Serotec (Raleigh, N.C.) and is advertised as having more than 15 billion functional human antibody specificities. Another commercially available library comprises camelid derived antibodies and is available from Ablynx, Ghent, Belgium. These libraries have the advantage of not requiring any particular immunogen prior to screening. Screenings of this library may also be carried out as discussed above. The antibody of the present invention may take any form that is described for use in immunodetection or immunotherapy. For instance, the antibody may be polyclonal, monoclonal, chimeric, human, humanized, bispecific, multispecific, primatized or an antibody fragment. Antibody fragments that me be of use in the present invention may comprise but not be limited to is Fab, ScFv, Fab', F(ab')$_2$, Fv, Fv(ab)$_2$ or aggregates thereof.

The presence of a sulfonation group should in itself be sufficient to define part of an epitope. In an analogous fashion for another post-synthetic modification, the literature is replete with a large number of antibodies that are dependent on targets being either in phosphorylated or unphosphorylated forms and these form the basis of numerous assays for kinase activity. Furthermore, as described previously, the presence or absence of such small chemical moieties as a phosphate or sulfonate group can have profound effects upon activity, thus validating the ability of biological partners to be able to recognize the differences between modified and unmodified forms. Specific examples of the search and identification of antibodies that are specific to epitopes of target proteins comprising a sulfonated Tyrosine have been described by Bundgaard et al., cited above. In a further example, an antibody (Mab15) that was selected for recognizing thyrotrophin receptor (TSHr) was found to have an epitope that was only found in mature forms of its target protein suggesting that some form of processing was required to create the appropriate epitope (Costagliola et al., 2002 EMBO J 21; 504-513). In vivo treatment of cells with chlorate (which as mentioned earlier reduces sulfonation modifications) resulted in production of a mature protein that was now unrecognizable by Mab15 indicating that the antibody was able to distinguish between the sulfonated and unsulfonated forms of its epitope and would only bind to the sulfonated version. Thus, even though it was not originally selected for this feature, the use of sulfonated antigens allowed isolation and identification of an antibody specific for a sulfonate epitope in this target.

Although peptides may be used for the generation of linear epitopes, antibodies can also be found that recognize a three-dimensional set of determinants (sometimes referred to as interrupted epitopes or non-linear epitopes) and development and isolation of these types of antibodies can be carried out by using three-dimensional antigens such as the entire protein of interest or selected fragments as immunogens. Such antibodies may also be realized from screening of pre-formed libraries that are independent of an immunogen. Screening can then be carried out for an ability to distinguish between sulfonated and unsulfonated versions of the protein of interest. For a discussion on the use of conformationally derived epitopes, see Van Regenmortel 1998, J Immunol Methods 216; 37-48, Villen et al., 2001 Biologicals 29; 265-269, Moreau et al., 2006 Bioinformatics 22; 1088-1095 and Huang and Honda 2006 BMC Immunology 7; 7.

In addition to acting as pharmacological agents, the development of antibodies directed against the sulfonation site of Sclerostin, may also find use for analytical or diagnostic purposes for evaluating the presence of sulfonated proteins and/or the extent of sulfonation. As described previously, shifts in the level of sulfonation levels has previously noted to be a feature of gastrin and cholcystokinin in cancer cells (Rehnfeld, 1990). The protein samples may be products that are excreted in the media or they may be derived from cell extracts. By these means, evaluation of physiological levels of sulfonation of Sclerostin can be carried out with biological specimens. These may be used in a variety of ways to compare specimens that differ from each other in terms of origin, treatment or physiological conditions. An antibody specific for a sulfonated form of a target protein may be used alone for this purpose or it may be combined in an assay that further includes an antibody directed towards the unsulfonated form or an antibody that recognizes both sulfonated and unsulfonated forms. In reference to the latter, an ability to recognize both sulfonated and unsulfonated forms may be a property of an antibody that recognizes the epitope where the sulfonation is located but is generically independent of the sulfonation state, or it can an antibody that lacks relevance to the sulfonation state by recognizing an epitope that is located outside of the modification region of Sclerostin.

As discussed above, antibodies of this nature may also be used to evaluate in vitro assays of sulfonation where they may be used to monitor conversion of the unsulfonated form into the modified form. These antibodies may also be used alone or in conjunction with antibodies that recognize an epitope specific for the unsulfonated form and/or for antibodies to an epitope in an amino acid sequence different from the sulfonation sequence. Thus, for instance, an antibody that is specific for the sulfonated form of Sclerostin may be used in conjunction with an antibody that is specific for an unsulfonated region of Sclerostin for normalization purposes. In another example of use, an antibody that is specific for the unsulfonated form can be used in conjunction with an antibody that recognizes the same region but essentially offers no discrimination between the sulfonated and unsulfonated forms of the antigen. Alternatively, two antibodies can be used where one is specific for the sulfonated form and another is for the unsulfonated form.

Furthermore, although the binding of Sclerostin to an LRP receptor is responsible for biological effects, it is also known that Sclerostin interacts with other proteins such as BMPs (Bone Morphogenic Proteins) (Winkler et al., 2003 EMBO J 22; 6267-6276), Noggin (Winkler et al., 2004 J Biol Chem 279; 36293-36298) and "Cysteine-rich protein 61" (Craig et al 2010 (BBRC 392; 36-40). As such, the discovery of the sulfonated amino acids in Sclerostin allows application of the present invention to interactions between Sclerostin and these other proteins as well as the interactions with LRP receptors. Additionally, although the Tyrosine modifications have been discussed in terms of alterations of a Sclerostin's affinity for a binding partner in a heterodimeric interaction, dimerization is also an example of a protein/protein interaction and as such, a homodimeric Sclerostin interaction may also be influenced by sulfonation modifications, and Sclerostin itself, should be included in the potential list of binding partners for Sclerostin. The degree of dimerization may have further effects with regard to binding to other proteins, where the affinity of a dimeric protein may be higher than that of a monomeric form. For instance, see Jekel et al., Biochimica Biophica Acta 1996 1291; 195-198 where the affinity of a dimerized antigenic peptide is higher than the monomeric form with regard to binding to an antibody. In another instance, TNF-α exists in trimeric form and binds to three receptors simultaneously (Banner et al., 1993, Cell, 73:431-445). Since dimerization or multimerization of proteins may be affected by sulfonation processes, the methods above may also be applied to homodimeric interactions when the ability of a compound to affect sulfonation is being analyzed. Assays that measure the ability of sulfonated and unsulfonated Sclerostin to form a complex with a binding partner may also be carried out with another Sclerostin molecule as the intended binding partner. Antibodies may also be developed that are specific to dimers as compared to monomers as previously described by Raven et al., in US Patent application No. 20050163776. Selectivity may be carried out by testing for the ability to react with dimers and then counter-selecting by eliminating antibodies that exhibit cross-reactivity with the monomeric form.

Antibodies directed against sulfonation sites in Sclerostin and pharmaceutical agents that disrupt or inhibit sulfonation of Sclerostin may find therapeutic utility with a variety of "Sclerostin-related disorders". The compositions and methods of the present invention are particularly suitable for treating, preventing or diagnosing Sclerostin-related disorders and/or aberrant bone mineral density disorders, e.g., osteoporosis. Compositions of the present invention may also be useful for improving outcomes in orthopedic procedures, dental procedures, implant surgery, joint replacement, bone grafting, bone cosmetic surgery and bone repair such as fracture healing, nonunion healing, delayed union healing and facial reconstruction. One or more compositions may be administered before, during and/or after the procedure, replacement, graft, surgery or repair.

As used herein, "a Sclerostin-related disorder" includes disorders in which bone mineral density (BMD) is abnormally and/or pathologically low relative to healthy subjects. Disorders characterized by low BMD and/or bone fragility include but are not limited to primary and secondary osteoporosis, osteopenia, osteomalacia, osteogenesis imperfecta (01), avascular necrosis (osteonecrosis), fractures and implant healing (dental implants and hip implants), bone loss due to other disorders (e.g., associated with HIV infection, cancers, or arthritis). Other "Sclerostin-related disorders" include but are not limited to rheumatoid arthritis, osteoarthritis, arthritis, and the formation and/or presence of osteolytic lesions.

As used herein, "a Sclerostin-related disorder" includes conditions associated with or characterized by aberrant Sclerostin levels. These include cancers and osteoporotic conditions (e.g., osteoporosis or osteopenia), some of which overlap with "Sclerostin-related disorders" as defined herein. Sclerostin-related cancers can include myeloma (e.g., multiple myeloma with osteolytic lesions), breast cancer, colon cancer, melanoma, hepatocellular cancer, epithelial cancer, esophageal cancer, brain cancer, lung cancer, prostate cancer, or pancreatic cancer, as well as any metastases thereof.

A "Sclerostin-related disorder" can also include renal and cardiovascular conditions, due at least to Sclerostin's expression in the kidney and cardiovasculature. Said disorders include but are not limited to such renal disorders as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, polycystic kidney disease, neoplasia, sickle cell disease, and chronic inflammatory diseases), tubular diseases (e.g., acute tubular necrosis and acute renal failure, polycystic renal diseasemedullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, gout, vascular diseases (e.g., hypertension and nephrosclerosis, microangiopathic hemolytic anemia, atheroembolic renal disease, diffuse cortical necrosis, and renal infarcts), or tumors (e.g., renal cell carcinoma and nephroblastoma).

Said disorders also include but are not limited to such cardiovascular disorders as ischemic heart disease (e.g., angina pectoris, myocardial infarction, and chronic ischemic heart disease), hypertensive heart disease, pulmonary heart disease, valvular heart disease (e.g., rheumatic fever and rheumatic heart disease, endocarditis, mitral valve prolapse, and aortic valve stenosis), congenital heart disease (e.g., valvular and vascular obstructive lesions, atrial or ventricular septal defect, and patent ductus arteriosus), or myocardial disease (e.g., myocarditis, congestive cardiomyopathy, and hypertrophic cariomyopathy).

According to a further embodiment of the invention, the antibodies and other pharmacological agents of the present invention may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, calcilytics, calcimimetics (e.g., cinacalcet), a steroid hormone, e.g. an estrogen, a partial estrogen agonist or estrogen-gestagen combination, a SERM (Selective Estrogen Receptor Modulator) e.g. raloxifene, lasofoxifene, bazedoxifene, arzoxifene, FC1271, Tibolone (Livial®), a SARM (Selective Androgen Receptor Modulator), a RANKL antibody (such as denosumab), a cathepsin K inhibitor, vitamin D or an analogue thereof or PTH, a PTH fragment or a PTH derivative e.g. PTH (1-84) (such as Preos™), PTH (1-34) (such as Forteo™), PTH (1-36), PTH (1-38), PTH (1-31)NH2 or PTS 893. According to another embodiment, the antibodies of the invention may be employed in combination with other current osteoporosis therapy approaches, including bisphosphonates (e.g., Fosamax™ (alendronate), Actonel™ (risedronate sodium), Boniva™ (ibandronic acid), Zometa™ (zoledronic acid), Aclasta™/Reclast™ (zoledronic acid), olpadronate, neridronate, skelid, bonefos), statins, anabolic steroids, lanthanum and strontium salts, and sodium fluoride. When pharmacological agents of antibodies of the present invention are administered together with another agent, the two can be administered in either order (i.e. sequentially) or simultaneously.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1 In Vitro Sulfonation of Sclerostin

Human Sclerostin (25 µg R&D Systems, Minneapolis, Minn.)) was reconstituted in 100 µl of 100 mM MES pH=7.0. Sulfonation was carried out by mixing 50 µl (12.5 µg) human Sclerostin and 22.5 µl (10.0 µg) of human TPST1 (R&D Systems) with 125 µL of assay mix [78.87 mM MES pH=7.0, 2.5 mM MgCl$_2$, 2.5 mM MnCl$_2$ 1.25 mM CaCl$_2$ and 200 µM PAPS (Sigma)]. Incubation was carried out for 1.5 hrs at 37° C. Buffer was then exchanged into 10 mM Tris pH=7.5 using protein desalting spin columns (Pierce Biochemicals, Rockford, Ill.).

Example 2 Detection of Sulfonation Modifications by MS Analysis

Peptides from the Sclerostin from Example 1 as well as untreated Sclerostin was digested with either trypsin or GluC and loaded onto a C18 column followed by injection into a LTQ mass spectrometer. In the first analysis, the mass spectrometer was instructed to make MS/MS of all eluting peptides. The resulting data was analyzed and three peptides from Sclerostin containing tyrosines were identified: LGEYPEPPPELE (SEQ ID NO: 1), YVTDGPCR (SEQ ID NO: 2) and ANQAELENAY (SEQ ID NO: 3). In the second analysis, targeted analysis was performed where the mass spectrometer was instructed to only do MS/MS on masses corresponding to the putative sulfonated tyrosine containing peptides. For the GluC sample, the mass spectrometer was set to perform MS/MS at m/z 725.6, the mass of the doubly charged peptide LGEYPEPPPELE (SEQ ID NO: 1) plus sulfation, at a normalized collision energy for CID at 2%, 4% or 10% and an MS3 of the highest fragment in each of the three MS/MS. In the tryptic sample, MS/MS was performed at m/z 602.0, the mass of the doubly charged peptide ANQAELENAY (SEQ ID NO: 3) plus sulfonation, and at m/z 524.5, the mass of the doubly charged peptide YVT-DGPCR (SEQ ID NO: 2) plus sulfonation, at a normalized collusion energy for CID at 2%, 4% and 10% and an MS3 of the highest fragment in each of the three MS/MS. Both peptides at m/z 725.6 and 602.0, corresponding to sulfonated peptide LGEYPEPPPELE (SEQ ID NO: 1) and ANQAELENAY (SEQ ID NO: 3), respectively, showed a neutral loss of 80 Da (40 Da for a 2+ ion) at 10% CE which suggests that these peptides were sulfonated, whereas at 2% and 4%, the loss was not very pronounced (see FIG. 1). The neutral loss fragments were subsequently fragmented and produced the expected MS/MS for the expected peptides. The MS/MS at m/z 524.5 did not show such a loss (data not shown). Essentially the same results were seen for both the untreated sclersotin and the Sclerostin from Example 1 indicating the presence of sulfonation modifications in Sclerostin prior to the in vitro reaction with TPST-1 in Example 1. Furthermore, although a phosphate addition at this site would also result in a shift of ~80 kd higher weight, further tests showed that the modifications at these sites exhibited the chemical lability typical of a sulfonation modification.

Example 3 Biological Effects of In Vitro Sulfonation of Sclerostin

A) Effects of Sulfonation on Binding of Sclerostin to LRP5
1) Preparation of AlkPhos Labeled LRP5
293T cells were seeded into 9 cm dishes. The next day, each dish was transfected with 12 µg of LRP5R1/2AP construct using Lipofactamine Plus (Invitrogen, Carlsbad, Calif.) according to the manufacturer's instructions. LRP5R1/2-AP is a nucleic acid construct that expresses LRP5 extracellular domains 1 and 2 fused to alkaline phosphatase. 48 hours after transfection, the supernatant of the culture was collected as LRP5R1/2AP conditioned medium and concentrated 20 times using a Centricon unit (Millipore, Billerica, Mass.) and stored at −80° C.
2) Binding of AlkPhos-LRP5 to Sclerostin
Various amounts of unmodified Sclerostin or the in vitro treated Sclerostin from Example 1 were diluted into 80 µl of TBST buffer and added to individual wells of 96 well plates. After overnight incubation, unbound proteins were removed after which point the coated plates were blocked with 3% nonfat milk in PBS. The plates were than decanted and 0.5×LRP5R1/2AP conditioned medium was added to the plates. After 2.5 hours, the conditioned medium was removed and the 96 well plates were washed five times for three minutes with TBST. The Alkaline Phosphatase activity in each well was then determined using the Tropix luminescence assay kit (Invitrogen, Carlsbad, Calif.).
3) Results of the Binding Assay
As seen in FIG. 2, the Sclerostin treated in vitro with TPST showed a marked increase in the amount of AlkPhos-LRP5 bound to the plates when compared to the untreated Sclerostin. These results are best interpreted as evidence that there is an increase in the binding affinity of the treated protein compared to the starting material. These comparative results were repeated with the mouse versions of Sclerostin (not shown) and showed essentially similar results although the basal levels of the proteins were different for each source.

B) Effects of Sulfonation on the Ability of Sclerostin to Block Wnt Induced Expression of Alkaline Phosphatase
1) Induction of Alkaline Phophatase Activity
Growing cultures of 10T1/2 cells were washed with PBS and trypsinized for 5 minutes. Cells were resuspended at a concentration of 6×10$^5$ cells/ml and 10 µl were seeded into individual wells of a Costar 96 well plate (Corning, Inc.). Wnt 3a and either the untreated Sclerostin or the Sclerostin from Example 1 were added and the plates were incubated at 37° C. for 24 hours. 50 µl of universal lysis buffer (from the Luciferase Reporter Gene Assay, Roche Applied Science, Indianapolis, Ind.) was added to each well at ambient temperature for 5 minutes. Detection of alkaline phosphatase was measured by the addition of 50 µl of ready-to-use CPSD with Sapphire Enhancer (Applied Biosystems) followed by an incubation at ambient temperature for 25 minutes.
2) Results of the Assay
As seen in FIG. 3, the Sclerostin sulfonated in Example 1 gave similar results compared to the untreated Sclerostin except at the highest level of Sclerostin input where there was a significantly (P=0.006) more efficient blockage of Wnt induced alk phos activity. This result for the highest level of Sclerostin may be a result of the increase in the binding affinity of the treated protein compared to the starting material as seen in FIG. 2.
It should be noted that the Sclerostin used in these experiments was derived from recombinant clones in mammalian cell lines. Consequently, as seen in the MS results in Example 2, there is a significant population of Sclerostin proteins that already have pre-existing sulfonation modifications. Thus, the positive effects seen in the experiments above is the result of conversion of any remaining unsulfonated forms into the sulfonated version by TSPT-1.

Example 4 Evaluation of Sclerostin Sequences with "Sulfinator" Program

The "Sulfinator" program is an online methodology of predicting the presence of sites in proteins that are substrates for tyrosine sulfonation (Monigatti et al. 2002 Bioinformatics 18; 769-770). When this program was applied to the human Sclerostin sequence (UniProtKB Accession No. Q9BQB4), the amino acid sequence ELGEYPEPP-PELENNK (SEQ ID NO: 4) in the N terminal region of Sclerostin was identified as corresponding to a Tyrosine sulfonation site with sulfonation taking place with Tyros in agreement with the MS results from Example 2. The corresponding sequences in the mouse and rat are GLGEYPEP-PPENNQTM (SEQ ID NO: 5) and GLREYPEPPQELENN Q (SEQ ID NO: 6), respectively (UniProtKB Accession No Q99P68 and Q99P67) where differences in the amino sequence are underlined. Evaluation of the mouse and rat Sclerostin sequences by the Sulfinator program revealed that the rat protein should also be sulfonated (and at the corresponding Tyr residue) while the mouse sequence did not show a positive result. It should be noted, however, that part of the criteria used by the Sulfinator program is contextual neighboring amino acid sequences and when the oligopeptide GLGEYPEPPPENNQTM (SEQ ID NO: 5) from the mouse Sclerostin sequences was independently tested, it was indicated as being potential site for sulfonation. The loose structure at the amino terminal end of Sclerostin (to be discussed below) is likely responsible for the oligopeptide Sulfinator results of mouse Sclerostin being in agreement with the binding assay results.

The region of Sclerostin involved in binding to LRP5/6 is not precisely known. It has been described as "Finger 2" (~aa's 115-147) by Weidauer et al., (2009 BBRC 380; 160-165) and "Loop 2" (~aa's 86-112) by Veverka et al., (2009 JBC 284; 10,890-10,900) where amino assignments are based on the mature protein. It can be seen that neither putative location corresponds to the $Tyr_{43}$ site. Nonetheless, a visualization of the predicted 3-dimensional structure shows that $Tyr_{43}$ is part of a loosely organized peptide strand that could located in proximity with the binding site in "loop 2" predicted by Ververka et al. As such, it is possible that the amino terminal portion of Sclerostin also participates in binding of Sclerostin to LRP5/6 and sulfonation may have effects on this particular protein/protein interaction. Further support is from U.S. Pat. No. 7,585,501 where the $Tyr_{43}$ site is a short distance away from an additional Sclerostin sequence (#15) that was described as participating in binding with LRP5/6. This point is illustrated further in FIG. 4.

Example 5 Peptides Derived from Sulfonation Sites

Peptides from the sulfonation modification sites regions may be useful in modulating protein-protein interactions between a sulfonated protein and a binding partner. Thus, for example, the sequences ELGEYPEPPPELENNK (SEQ ID NO: 4) and KANQAELENAY (SEQ ID NO: 7) from Sclerostin can be used to artificially synthesize peptides that can be used as therapeutic compounds. Both modified and unmodified versions of these peptides can be made and tested to see which ones are more effective and if they are equivalent in potency.

Example 6 Development of Antibodies Specific for Sulfonated Proteins

Antibodies that are specific for Sclerostin can be developed using peptides derived from the recognition sequences described in Examples 2 and 5. In FIG. 4, the sites previously described for use as epitopes for Sclerostin antibodies is compared with the sulfonation sites described in Example 2. Unmodified peptides can be designed and obtained from numerous commercial sources. Post-synthetic modifications can then be carried out either chemically or by in vitro modification by TPST-1. These antigens can then be used to obtain antibodies using methods taught in Bundgaard et al., 2008; Hoffhiner et al., 2006 Kehoe et al. 2006, U.S. Pat. No. 7,585,501, US Patent application 2004/0009535 and US Patent Application 2009/02130113. Screenings can be carried out to determine the nature of the recognition such that it is specific for sulfonation of only the target protein. A similar program can be carried out with analogous peptides that remain unmodified; these can be used to obtain antibodies that are specific for the unmodified version of the targets. Screenings can also be based upon an ability to bind to the specific region of the Sclerostin sulfonation, but the affinity of the protein is for both sulfonated and unsulfonated versions of the antigen target.

The discovery of a sequence in Sclerostin that comprises a sulfonate modified Tyrosine provides information concerning previously unknown epitopes in Sclerostin that may be used to generate novel antibodies that target these sites. For this purpose, a peptide can be used that comprises the sequence ELGEYPEPPPELE (SEQ ID NO: 8) where the Tyrosine is modified to comprise a sulfonate group in order to generate an antibody that targets the sulfonated Tyrosine site at the amino end of Sclerostin. This modification can be carried out either chemically or by treatment with TPST-1 and PAPS. Another peptide, comprising the sequence KANQAELENAY (SEQ ID NO: 7) (where the Tyrosine is also modified by sulfonation) can be used to generate an antibody to the sulfonated Tyrosine site at the carboxyl end of Sclerostin. Generation and isolation of an antibody can then be carried out by the methods described by Bundgaard et al., 2008 in conjunction with the methods taught in U.S. Pat. No. 7,585,501, US Patent Application 20040009535 and US Patent Application 20090130113, all of which are incorporated by reference.

When using a peptide with a sulfonated Tyrosine as the immunogen, resultant antibodies can display a variety of different affinities. For example, in an article giving the protocol for generating antibodies against peptides containing a phosphorylated Tyrosine, the point is made: "Such an immunization will generate an immune response with at least four components: (1) anti-carrier protein reactivity, (2) general antiphosphotyrosine reactivity, (3) phosphorylation-independent anti-peptide reactivity and (4) phosphorylation-dependent anti-peptide reactivity." (DiGiovanna et al., 2002 Current Protocols in Cell Biology 16.6.1-16.6.18). As such, this article points out that even when using a peptide with the appropriate modification, antibodies can be generated that may only require the appropriate amino acid sequence and ignore the presence or absence of a modified Tyrosine. Consequently, many of the past efforts to isolate an antibody against a phoshphorylated peptide have included a counter-selection step to eliminate antibodies that bind to the unphosphorylated version of the target peptide/protein.

In contrast, although it is a goal of the present invention to generate and isolate antibodies that are specific for a protein that has a sulfonated tyrosine, utility is also found during such a search to identify and isolate antibodies that are specific for the sulfonated Tyrosine site but that are also independent of the sulfonation state of the target protein. Thus in parallel, identification processes can be carried out that initially are identified in terms of an the ability to bind to the region encompassed by the sulfonation modifications and then a secondary screening can be carried out for a) antibodies that have the ability to detect only epitopes that include the sulfonation modification and b) antibodies that are independent of the sulfonation status of the target region.

Many obvious variations will no doubt be suggested to those of ordinary skill in the art in light of the above detailed description and examples of the present invention. All such variations are fully embraced by the scope and spirit of the invention as more particularly defined in the claims that now follow.

What is claimed is:

1. A method for production of a monoclonal antibody specific for a sulfonation site in Sclerostin, comprising the steps of:

immunizing an animal with a synthetic peptide derived from the Sclerostin amino acid sequence, wherein said peptide comprises a sulfonation site in said Sclerostin that comprises a tyrosine corresponding to Tyr43 or Tyr213 of human Sclerostin;

isolating antibody producing cells from said immunized animal;

fusing the isolated antibody producing cells with myeloma cells to form antibody producing hybridoma cells; and screening the hybridoma cells to identify hybridoma cells that produce antibodies that discriminate between sulfonated and unsulfonated forms of said sulfonation site of Sclerostin.

2. The method of claim 1, wherein said tyrosine is sulfonated in the synthetic peptide.

3. The method of claim 1, wherein said tyrosine corresponds to Tyr43 of human Sclerostin.

4. The method of claim 3, wherein said tyrosine is sulfonated in the synthetic peptide.

5. The method of claim 1, wherein the synthetic peptide is selected from the group consisting of:
(a) ELGEYPEPPPELE (SEQ ID NO:8), wherein tyrosine is sulfonated;
(b) ELGEYPEPPPELE (SEQ ID NO:8), wherein tyrosine is not sulfonated;

(c) KANQAELENAY (SEQ ID NO:7), wherein tyrosine is sulfonated; and
(d) KANQAELENAY (SEQ ID NO:7), wherein tyrosine is not sulfonated.

6. The method of claim 5, wherein the peptide is ELGEYPEPPPELE (SEQ ID NO:8), wherein tyrosine is sulfonated.

* * * * *

SEQUENCE LISTING

<160> NUMBER OF SEQ ID NOS: 10

<210> SEQ ID NO 1
<211> LENGTH: 12
<212> TYPE: PRT

<213> ORGANISM: Homo sapiens

<400> SEQUENCE: 1

Leu Gly Glu Tyr Pro Glu Pro Pro Glu Leu Glu
1               5                   10

<210> SEQ ID NO 2
<211> LENGTH: 8
<212> TYPE: PRT
<213> ORGANISM: Homo sapiens

<400> SEQUENCE: 2

Tyr Val Thr Asp Gly Pro Cys Arg
1               5

<210> SEQ ID NO 3
<211> LENGTH: 10
<212> TYPE: PRT
<213> ORGANISM: Homo sapiens

<400> SEQUENCE: 3

Ala Asn Gln Ala Glu Leu Glu Asn Ala Tyr
1               5                   10

<210> SEQ ID NO 4
<211> LENGTH: 16
<212> TYPE: PRT
<213> ORGANISM: Homo sapiens

<400> SEQUENCE: 4

Glu Leu Gly Glu Tyr Pro Glu Pro Pro Glu Leu Glu Asn Asn Lys
1               5                   10                  15

<210> SEQ ID NO 5
<211> LENGTH: 16
<212> TYPE: PRT
<213> ORGANISM: Mus musculus

<400> SEQUENCE: 5

Gly Leu Gly Glu Tyr Pro Glu Pro Pro Glu Asn Asn Gln Thr Met
1               5                   10                  15

<210> SEQ ID NO 6
<211> LENGTH: 16
<212> TYPE: PRT
<213> ORGANISM: Rattus norvegicus

<400> SEQUENCE: 6

Gly Leu Arg Glu Tyr Pro Glu Pro Gln Glu Leu Glu Asn Asn Gln
1               5                   10                  15

<210> SEQ ID NO 7
<211> LENGTH: 11
<212> TYPE: PRT
<213> ORGANISM: Homo sapiens

<400> SEQUENCE: 7

Lys Ala Asn Gln Ala Glu Leu Glu Asn Ala Tyr
1               5                   10

<210> SEQ ID NO 8
<211> LENGTH: 13
<212> TYPE: PRT
<213> ORGANISM: Homo sapiens

```
<400> SEQUENCE: 8

Glu Leu Gly Glu Tyr Pro Glu Pro Pro Glu Leu Glu
1               5                   10

<210> SEQ ID NO 9
<211> LENGTH: 14
<212> TYPE: PRT
<213> ORGANISM: Homo sapiens

<400> SEQUENCE: 9

Glu Leu Gly Glu Tyr Pro Glu Pro Pro Glu Leu Glu Asn
1               5                   10

<210> SEQ ID NO 10
<211> LENGTH: 188
<212> TYPE: PRT
<213> ORGANISM: Homo sapiens

<400> SEQUENCE: 10

Trp Gln Ala Phe Lys Asn Asp Ala Thr Glu Ile Ile Pro Glu Leu Gly
1               5                   10                  15

Glu Tyr Pro Glu Pro Pro Glu Leu Glu Asn Asn Lys Thr Met Asn
            20                  25                  30

Arg Ala Glu Asn Gly Gly Arg Pro Pro His His Pro Phe Glu Thr Lys
            35                  40                  45

Asp Val Ser Glu Tyr Ser Cys Arg Glu Leu His Phe Thr Arg Tyr Val
            50                  55                  60

Thr Asp Gly Pro Cys Arg Ser Ala Lys Pro Val Thr Glu Leu Val Cys
65                  70                  75                  80

Ser Gly Gln Cys Gly Pro Ala Arg Leu Leu Pro Asn Ala Ile Gly Arg
            85                  90                  95

Gly Lys Trp Trp Arg Pro Ser Gly Pro Asp Phe Arg Cys Ile Pro Asp
            100                 105                 110

Arg Tyr Arg Ala Gln Arg Val Gln Leu Leu Cys Pro Gly Gly Glu Ala
            115                 120                 125

Pro Arg Ala Arg Lys Val Arg Leu Val Ala Ser Cys Lys Cys Lys Arg
            130                 135                 140

Leu Thr Arg Phe His Asn Gln Ser Glu Leu Lys Asp Phe Gly Thr Glu
145                 150                 155                 160

Ala Ala Arg Pro Gln Lys Gly Arg Lys Pro Arg Pro Arg Ala Arg Ser
            165                 170                 175

Ala Lys Ala Asn Gln Ala Glu Leu Glu Asn Ala Tyr
            180                 185
```